United States Patent [19]

Sunago

[11] Patent Number: 4,545,657

[45] Date of Patent: Oct. 8, 1985

[54] LASER BEAM SCANNING MIRROR FINELY ADJUSTED VIA JOYSTICK

[75] Inventor: Katsuyoshi Sunago, Osaka, Japan

[73] Assignee: Sumitomo Electric Industries, Ltd., Osaka, Japan

[21] Appl. No.: 396,205

[22] Filed: Jul. 8, 1982

[30] Foreign Application Priority Data

Jul. 10, 1981 [JP] Japan .................................. 56-108616

[51] Int. Cl.$^4$ ................................................ G02B 5/08
[52] U.S. Cl. .............................. 350/600; 219/121 LU; 248/479
[58] Field of Search ............... 350/288, 308, 293, 586, 350/281, 562, 486; 521/110; 219/121 LU, 121 LV, 121 LW; 248/479

[56] References Cited

U.S. PATENT DOCUMENTS

| | | | |
|---|---|---|---|
| 2,876,676 | 3/1959 | Morgan | 350/281 |
| 4,228,341 | 10/1980 | Zandberg | 219/121 L UX |
| 4,247,161 | 6/1981 | Unertl | 350/562 |
| 4,350,777 | 9/1981 | Henrichs et al. | 521/110 |

FOREIGN PATENT DOCUMENTS

2226481  12/1973  Fed. Rep. of Germany ...... 350/281

OTHER PUBLICATIONS

Higgins et al., "Adjustable Beam Reflector" IBM Technical Disclosure Bulletin, vol. 21, No. 8, Jan. 1978, pp. 3089-3090.

*Primary Examiner*—John K. Corbin
*Assistant Examiner*—D. Lewis
*Attorney, Agent, or Firm*—Sughrue, Mion, Zinn, Macpeak & Seas

[57] ABSTRACT

A laser beam scanning mechanism includes a joystick controlled reflecting member designed so as to eliminate play by directly contacting a joystick end with a concave surface of a mirror holder, where the radius of curvature of the concave surface is slightly varied from the effective length of the joystick.

7 Claims, 7 Drawing Figures

LASER BEAM SCANNING MIRROR FINELY ADJUSTED VIA JOYSTICK

BACKGROUND OF THE INVENTION

This invention relates to a laser beam scanning mechanism in which, in the operation of a laser knife under a microscope, a joystick is operated to change the laser irradiation position.

In a surgical operation using a laser knife, the operator shifts the point irradiated with the laser beam by operating a joystick back and forth or right and left while observing the vital tissues through a microscope.

The laser irradiation position is determined by the inclination angle of a mirror. A mechanism for controlling the motion of the stick to control the inclination of the mirror has been disclosed by the specifications of Japanese Patent Application Laid Open Nos. 111295/1977 and 106144/1980, for example.

In the former mechanism, a mirror for reflecting the laser beam is supported by a horizontal shaft, and a stand including the horizontal shaft is supported by a vertical shaft. Servo motors are coupled to the horizontal shaft and the vertical shaft, respectively, so that the mirror is turnable about both the horizontal shaft and the vertical shaft. The horizontal movement and the lateral movement of the joystick operate respective potentiometers. The rotational displacements of the servo motors are detected, to change the resistance of other potentiometers. The two sets of potentiometers form two bridge circuits, so that the servo motors are turned in one direction or the other in response to the movements of the stick, to thereby change the inclination angle of the mirror.

In such an electrical scanning mechanism, two servo motors must be set in the housing of the microscope. Furthermore, since two orthogonal movements are required, two rotary shafts must be provided. Thus, the former mechanism is disadvantageous in that it is intricate in construction and accordingly costly.

On the other hand, the mechanism disclosed by Japanese Patent Application Laid-Open No. 106144/1980 is purely mechanical, employing a gimbal mechanism.

This mechanism is similar to the above-described mechanism in that the mirror is supported by a horizontal shaft, and a U-shaped stand including the horizontal shaft is supported by a vertical shaft, so that the mirror can turn about these shafts. However, it should be noted that, in this mechanism, instead of the servo motors and the potentiometers, several levers are used in combination so that the horizontal and vertical motions of the joystick are transformed into rotational displacements around the vertical and horizontal shafts, respectively.

Such a gimbal mechanism needs no servo motor; however, it requires two orthogonal rotary shafts and several levers in combination. Therefore, the housing of the microscope is necessarily bulky.

It is impossible to transmit the horizontal and vertical movements of the joystick to two rotary shafts through the same number of levers. Therefore, it is difficult to determine the speed-up ratio and the speed-down ratio of the "lever", to thereby make the horizontal and vertical movements coincident with the rates of rotational displacement of the mirror in the horizontal and vertical directions, respectively.

In order to operate orthogonal levers, a pin and an elongated hole must be employed in combination. In this combination, backlash is taken into account, and accordingly, the levers are subject to play. Since the number of levers in the vertical direction is different from that in the horizontal direction, accordingly the amount of play in the vertical direction is different from that in the horizontal direction.

Furthermore, the mechanism suffers from a difficulty in that, although two independent "lever" systems are required in order to transmit the horizontal and vertical movements to the mirror, the inclination of the mirror is not made independent. For instance, when the rotational displacements of the mirror about the horizontal shaft are different, and the stick is moved to the right and to the left with one and the same amplitude, the amounts of the displacement of the mirror about the vertical shaft are different from one another.

The most serious drawback is that, as the mirror is turned around the horizontal and vertical shafts through levers having a large amount of play, it is impossible to finely displace the mirror.

During a surgical operation under microscope, it is essential to finely shift the laser beam irradiation position. When the angle of inclination of the mirror is changed, the laser beam reflected by the mirror is deflected through an angle which is twice the change in the inclination angle of the mirror. The irradiation position is shifted by a value which is obtained by multiplying the angle of deflection by the distance between the mirror and the tissue being operated upon.

Thus, in order to finely control the laser beam irradiation position, it is essential that the inclination angle be finely controlled.

In the gimbal mechanism using the levers, it is difficult to sufficiently reduce the movement of the joystick to thereby change the angle of inclination of the mirror.

As is apparent from the above description, in the conventional mechanism, the reflecting mirror is rotatably supported by two orthogonal axes. Therefore, it has been impossible to reduce the size of the microscope's bulky housing.

In the case of a purely mechanical transmission mechanism, play takes place at all times, and it is difficult to finely adjust the inclination angle of the mirror. On the other hand, the electrical transmission mechanism suffers from the drawback that the microscope's housing is bulky and the resulting device has low operability.

SUMMARY OF THE INVENTION

An object of this invention is thus to provide a laser beam scanning mechanism in which the movement of the joystick is purely mechanically converted into a change in the angle of inclination of the mirror, wherein the construction is simple, but free from play, the conversion ratio in the horizontal direction is equal to that in the vertical direction, and wherein the mirror can be finely displaced.

In the laser beam scanning mechanism, a concave surface is formed in the rear wall of a mirror holder supported at the fulcrum which is the center thereof, the end of the joystick is in contact with the concave surface, and the distance (l) between the end of the stick and the fulcrum of the stick is made different from the radius of curvature (r) of the concave surface, so that the angle of inclination of the mirror is changed according to the movement of the joystick.

DETAILED DESCRIPTION OF THE PREFERRED EMBODIMENTS

Figure 1:
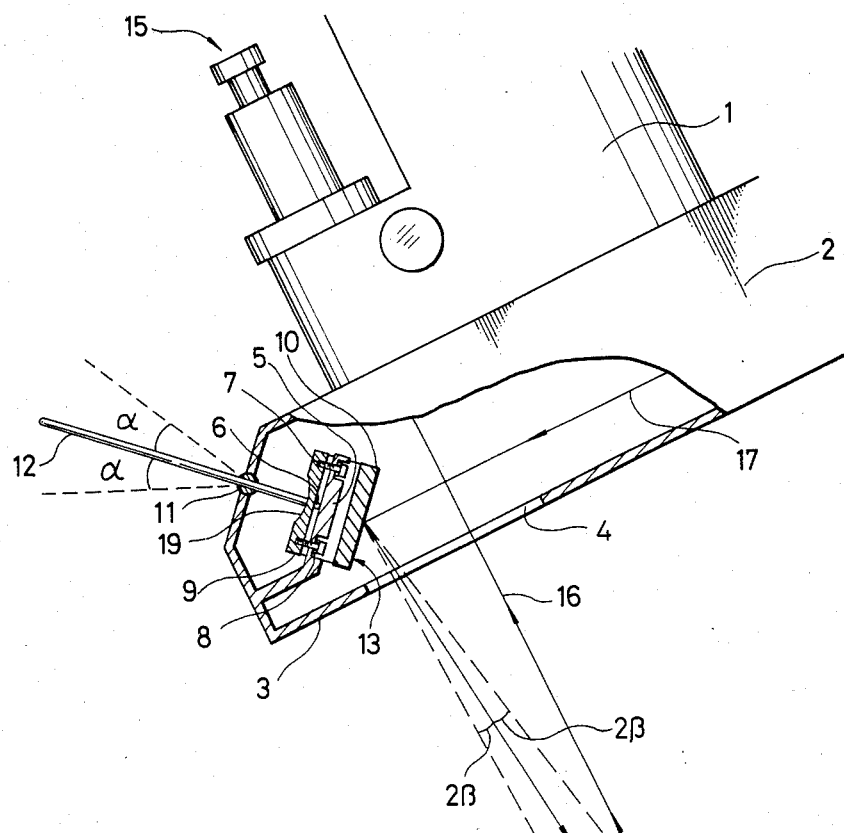
FIG. 1 is a sectional view showing one example of a laser beam scanning mechanism according to this invention.

FIG. 1 is a diagrammatic section view showing one example of a laser beam scanning mechanism according to the invention.

The laser beam scanning mechanism, as shown in FIG. 1, is incorporated in an adaptor 2 secured to the lower end of a microscope body 1. An adaptor body 3 is in the form of a box having an opening 4 in the lower surface. A supporting plate 5 extends obliquely from the near wall of the adaptor body 3. A small fulcrum ball 6 is provided on the supporting plate 5. At least three bolts 7 and at least three springs 8 are arranged rotationally symmetrically about the fulcrum ball 6, so that a mirror holder 9 can be tilted slightly about the fulcrum ball 6. A mirror 10 for reflecting the laser beam is provided in front of the mirror holder 9.

A joystick 12 is provided through a spherical bearing 11 on an upper wall of the adaptor body 3 in such a manner that it is horizontally and vertically movable.

The laser beam reflected by the mirror surface 13 is applied to a desired part of the tissue 14. That part of the tissue 14 thus irradiated can be observed through an eye piece 15. The microscope optical axis 16 extends from the tissue 14 through the opening 4 to the eye piece 15.

An incident laser beam 17 is maintained unchanged in direction and position, while the reflected laser beam 18 undergoes angular displacement as the angle of the mirror is changed.

A concave surface 19 (FIG. 3) having a radius of curvature r is formed in the rear surface of the mirror holder 9. The joystick 12 is rockable with one end thereof being in contact with the concave surface 19. If the effective length l of the stick (which is the distance between the spherical bearing 11 and the end of the stick 12) is different from the radius of curvature r of the concave surface, then the angle of inclination of the mirror holder 9 can be changed by operating the stick.

When the joystick 12 is moved through an angle $\alpha$, the mirror is tilted through an angle $\beta$. In this case, the reflected laser beam 18 is swung through an angle 2$\beta$.

Figure 2:
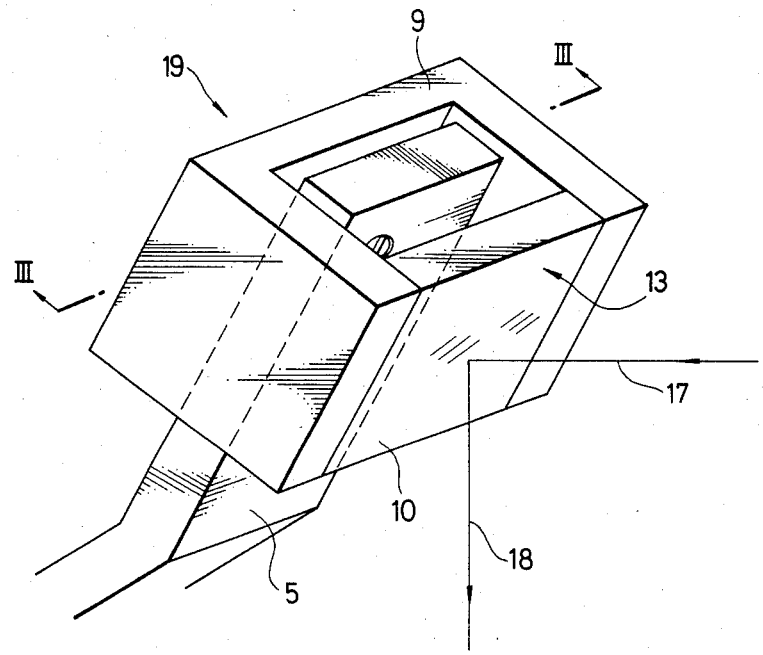
FIG. 2 is a perspective view of a mirror holder supporting mechanism.
Figure 3:
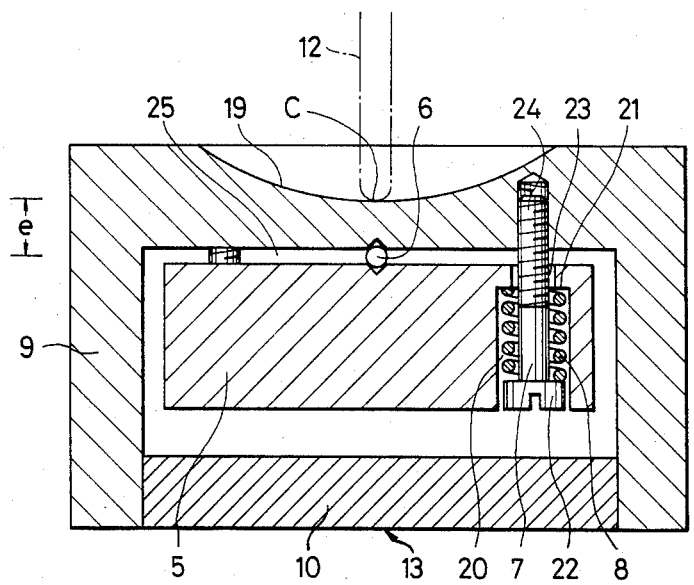
FIG. 3 is a sectional view taken along line III—III of FIG. 2.

One example of an elastic supporting mechanism for the mirror holder 9 and the supporting plate 5 are as shown in FIGS. 2 and 3.

The mirror holder 9 and the mirror 10 are assembled into one unit which is substantially in the form of a quadrangular prism. The mirror 10 is provided at the front surface of the quadrangular prism, and the concave surface 19 is formed in the rear surface thereof. The supporting plate 5 is inserted between the front and rear surfaces of the quandrangular prism, i.e., between the mirror 10 and the concave surface 19.

The bolts 7 are provided rotationally symmetrically about the fulcrum ball 6 of the supporting plate 5. A spring hole 20 is provided for each bolt. More specifically, the spring hole is bored in the supporting plate 5 at the position of each bolt 7. The spring 8 is inserted into the spring hole 20 in such a manner that it is compressed between the bolt head 22 and the step 21 in the spring hole 20.

The end portion of the bolt 7 is threadably engaged with a threaded hole 24 in the mirror holder 9 through a throughhole 23 in the supporting plate 5.

The mirror holder 9 is pulled towards the supporting plate 5 by means of the springs 8 and the bolts 7; however, there is a gap 25 between the mirror holder 9 and the supporting plate 5 because the fulcrum ball 6 is set therebetween.

When the end of the stick 12 is in contact with the center C of the rear surface immediately behind the fulcrum ball 6, the supporting plate 5 is parallel with the surface of the mirror holder 9. When, on the other hand, the end of the stick 12 pushes upon a point other than the center C, the mirror holder 9 is tilted because the radius of curvature r of the concave surface is different from the effective length l of the joystick.

Figure 4:
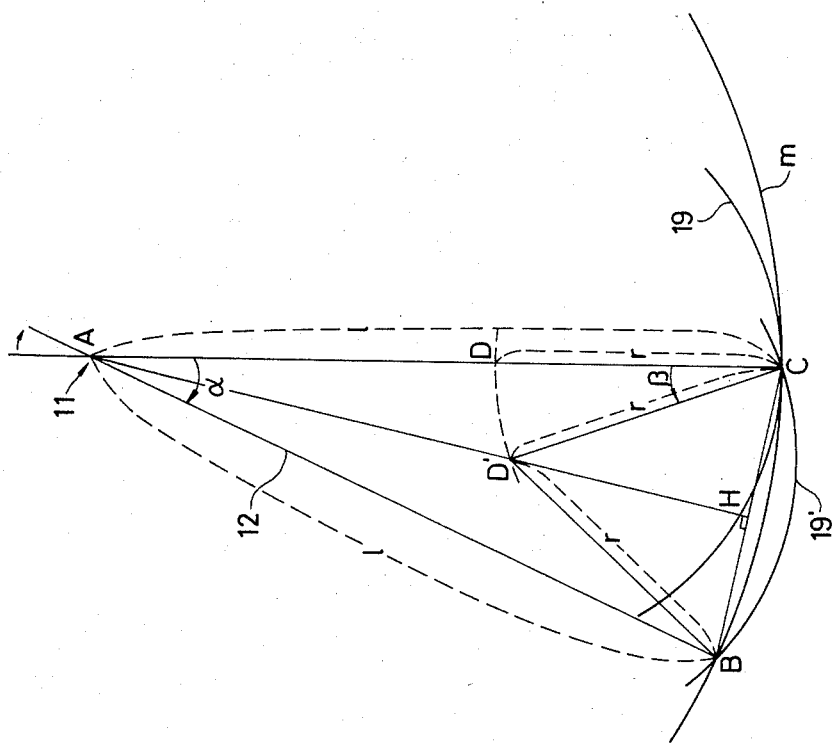
FIG. 4 is a diagram showing the relation between the movement of the joystick and the movement of a concave surface formed in the mirror holder, showing the case a>1.

FIG. 4 illustrates the arrangement of the stick 12 and the concave surface 19. The relation between the angle of inclination $\alpha$ of the stick and the angle of inclination $\beta$ of the mirror will be described with reference to FIG. 4.

In FIG. 4, reference numeral A designates the fulcrum of the stick 12, which corresponds to the center of the spherical bearing 11.

An arc m with a radius l and with the point A as its center is the locus of the end of the stick 12.

Thus, the center C of the arc m is the fulcrum of the concave surface 19. The center D of the concave surface 19 is located on the straight line AC, and CD=r (when the stick is disposed at the position AC).

FIG. 4 is for the case where the joystick's effective length l is larger than the radius of curvature r of the concave surface (l>r).

It is assumed that the stick 12 is moved until its end reaches a point B on the arc m. In this case, the inclination of the concave surface is as indicated at 19'. The concave surface passes through the end point B of the stick and the fulcrum C. Therefore, the center of the concave surface is moved to a point D' which is on the perpendicular bisector of the segment BC and satisfies CD'=r.

The locus of the center of the concave surface is a broken line DD'.

In this case, the angle of inclination of the concave surface is ∠D'CD, and $$\angle BAC = \alpha \qquad (1)$$

$$\angle D'CD = \beta$$

If it is assumed that the extension of the the straight line AD' intersects the straight line BC at a point H, then $$AB = AC = l \quad (3)$$

$$D'B = D'C = r$$

Therefore, both points A and D' are on the perpendicular bisector of the segment BC. Accordingly, the point H is the midpoint, and $\angle AHC = 90°$.

When the sine rule is applied to the triangle of AD'C:

$$\frac{r}{\sin \frac{\alpha}{2}} = \frac{l}{\sin\left(\frac{\alpha}{2} + \beta\right)} \quad (5)$$

From equation (5), the angle of inclination $\beta$ of the mirror is:

$$\beta = \sin^{-1}\left(\frac{l \sin \frac{\alpha}{2}}{r}\right) - \frac{\alpha}{2} \quad (6)$$

The ratio of the effective length l of the joystick to the radius of curvature r of the concave surface is set to $a \neq 1$, because if $a = 1$, $\beta = 0$.

With $$a = l/r \quad (7),$$

expression (6) can be written as follows:

$$\beta = \sin^{-1}(a \sin \alpha/2) - \alpha/2 \quad (8).$$

The above-described calculation is for FIG. 4, where $l > r$; however, it should be noted that the same equation can be obtained in the case $l < r$.

Figure 5:
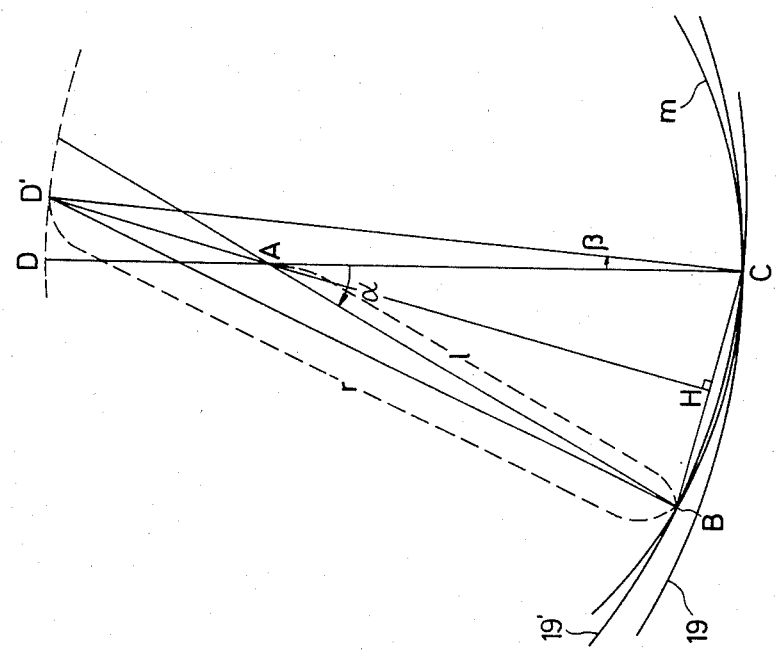
FIG. 5 is a diagram similar to that of FIG. 4, showing the case a<1.

FIG. 5 is for the case $l < r$. In FIG. 5, the point A is the stick fulcrum, and $AB = AC = l$. The points D or D' is the center of the concave surface, and the straight line D'AH is the perpendicular bisector of the segment BC. However, it should be noted that the sign of $\beta$ is different from that of $\alpha$. The angle $\beta$ should be defined toward the same side as the angle $\alpha$. In FIG. 5, the angle $\alpha$ is measured towards the left-handed side from the center line AC, and therefore the angle $\alpha$ has the positive sign. On the other hand, as the angle $\beta$ is measured towards the right-handed side, the angle $\beta$ is negative.

If the definition of the angles $\alpha$ and $\beta$ include the signs also, the relation between $\alpha$ and $\beta$ can be represented by equations (6) or (8) irrespective of the difference between the parameters l and r.

When $\alpha/2$ is much smaller than one (1), the following expression (9) can approximate the expression (8):

$$\beta = (a - 1) \times \alpha/2 \quad (9)$$

For instance when $a = 0.9$, $$\beta = \alpha/20 \quad (10)$$

That is, with the angle of inclination of the stick reduced by the ratio 20:1, the angle of inclination of the mirror can be finely changed. The reduction ratio of the angle variation (R) is as follows:

$$R = 2/(a - 1) \quad (11)$$

Accordingly, as the parameter a is made closer to one (1), the motion of the mirror can be more finely adjusted.

Figure 6:
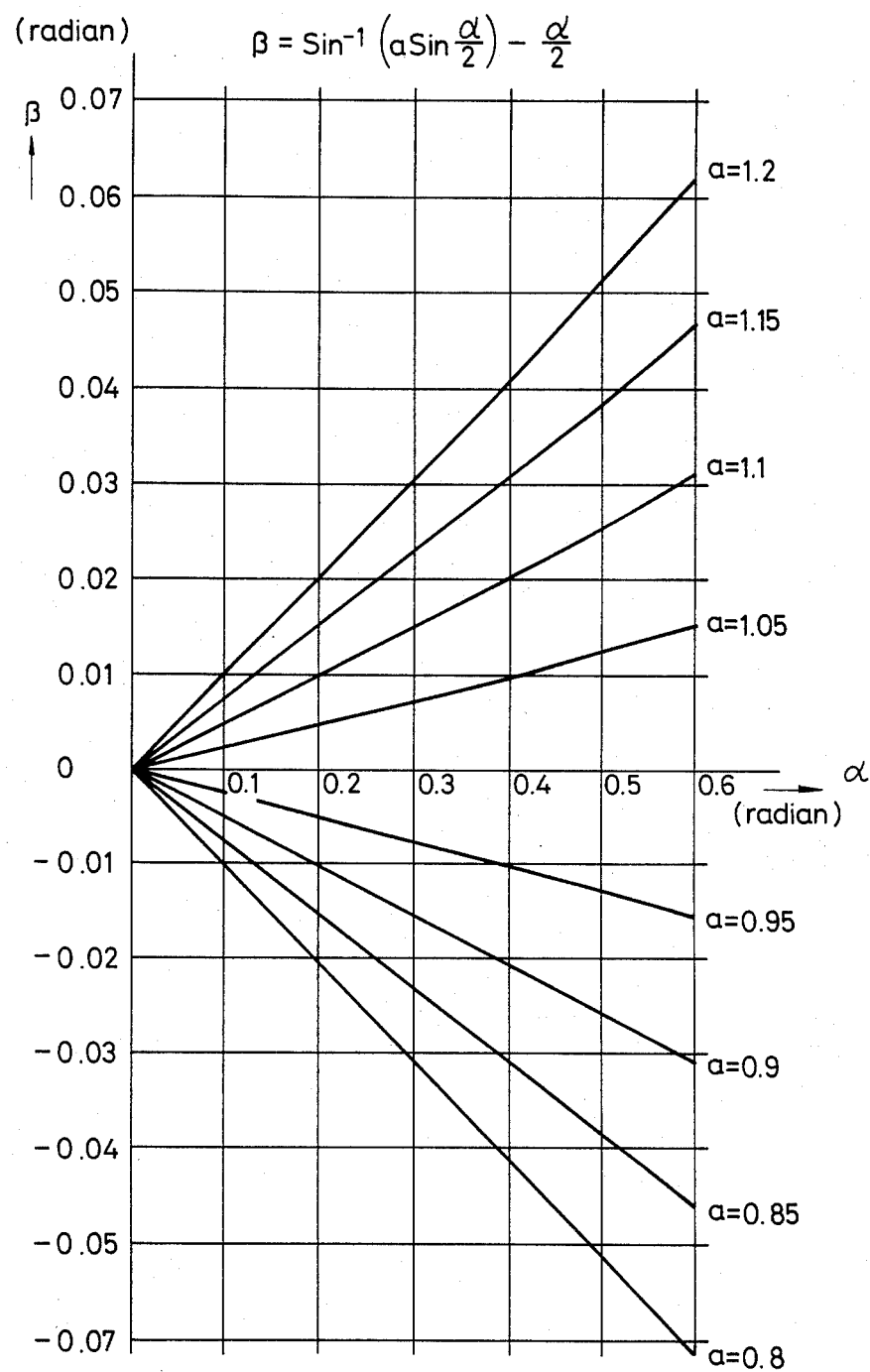
FIG. 6 is a graphical representation indicating the relationship between the angles of inclination $\alpha$ of the joystick and the angles of inclination $\beta$ of the concave surface, with a as parameter; and, FIG. 7 is a sectional view showing another example of the elastic supporting mechanism of the mirror holder.

FIG. 6 is a graphical representation indicating the angles of inclination $\alpha$ of the stick and the angles of inclination $\beta$ of the mirror with a as the parameter. In FIG. 6, eight values 0.8, 0.85, 0.9, 0.95, 1.05, 1.1, 1.15, and 1.2 are selected for the parameter a.

The angle of inclination $\alpha$ of the joystick is up to 0.6 radian (34.4°). It can be understood that, in this range, $\beta$ changes linearly with 60.

The angle of inclination of the mirror has been described above. In this connection, the angle of deflection of the reflected laser beam is $2\beta$, because it is twice the inclination angle of the mirror.

If the distance between the mirror surface to the tissues is represented by L and the irradiation position on the tissue is represented by x, then the ratio of scanning position displacement with respect to the stick operation can be defined as follows:

$$\frac{dx}{d\alpha} = 2L \frac{d\beta}{d\alpha} \quad (12)$$

In the case where $\alpha/2$ is much smaller than one (1), similarly as in the case of expression (9), expression (12) can rewritten as follows:

$$\frac{dx}{d\alpha} = L(a - 1) \quad (13)$$

If a is made close to one (1), the variation of the irradiation position x can be made considerably small.

The effects of the invention are as follows:

(1) As the laser beam scanning mechanism of the invention is considerably simple in construction, the housing of the adapter to the microscope can be miniaturized by as much.

(2) The laser beam irradiation position can be finely adjusted, because the ratio of the angle of inclination $\beta$ of the mirror to the angle of inclination $\alpha$ of the joystick is smaller as the ratio of the stick effective length l to the radius of curvature r of the concave surface approaches unity.

(3) Since no levers or gears are used, no play is involved. In order to obtain fine displacement, it is desirable that the power transmitting system be free from play. In the invention, there is no play between fulcrum ball, the supporting plate and the mirror holder, and there is no gap between the end of joystick and the concave surface.

(4) A method in which the motion of the joystick is transmitted to the mirror after being divided into horizontal and vertical components is not employed in the invention. The motion of the stick is equivalent in all directions, and the curvature of the concave surface is the same in all directions.

Accordingly, the mirror is considerably smoothly movable, and the horizontal reduction ratio is in agreement with the vertical reduction ratio at all times.

Figure 7:
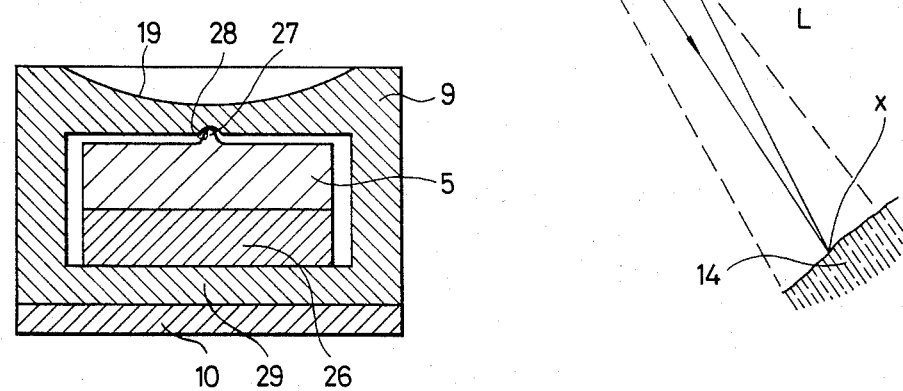

In combining the supporting plate 5 with the mirror holder 9, (1) it is necessary that they be supported by means of the fulcrum ball 6, i.e., one point, and (2) it is essential for the mirror holder 9 to be elastically pushed towards the fulcrum ball. Therefore, at least three bolts and at least three springs are provided as described above. In addition, a rubber member 26 may be interposed between the supporting plate 5 and the wall of the mirror holder opposite the wall in which the concave surface has been formed. (FIG. 7). Furthermore, in order to provide a fulcrum for the supporting plate and the mirror holder, a protrusion 27 and a recess 28 for receiving the protrusion 27 may be provided for the supporting plate 5 and the mirror holder 9, respectively, or vice versa. The arrangement of the elastic supporting mechanism is optional.

In the case where the mirror holder 9 is in the form of a rectangular prism, the mirror 10 may be bonded to one surface 29 thereof.

In the above-described laser beam scanning mechanism, the concave surface 19 and the mirror 10 are provided on the opposite walls of the mirror holder, respectively; however, if the joystick mounting position is changed, then the concave surface 19 and the mirror 10 may be provided on adjacent walls of the mirror holder.

The fulcrum of the mirror holder must be near the center of the concave surface. With the distance e between the center of the fulcrum ball 6 and the concave surface center C as shown in FIG. 3, it is unnecessary to add serious correcting terms to equations (6) and (8).

The value a may be larger than one or may be smaller than one. In the case of FIG. 1, the value a must be larger than one (a>1) so that, when the stick 12 is moved to the right-handed side, the irradiation point x is moved in the same direction, because the parameters $\alpha$ and $\beta$ have the same sign (according to expression (8)). In the case where the microscope forms the erecting image of the object, it is preferable that the value a be larger than one (1), because the positional relationship can be known by intuition.

If a<1, the direction of the movement of the joystick is opposite to the direction of movement of the irradiation point x. Thus, in the case where the microscope forms an inverted image of the object, it is preferable in operation that the value a be smaller than one (a<1).

What is claimed is:

1. A laser beam scanning adjustment mechanism in which the movement of a joystick is transformed into the inclination of a mirror, comprising;
    a movable mirror holder for holding a mirror, said mirror holder having a concave surface with a first point substantially at the center of said concave surface, pivot bearing means positioned between said mirror holder and said mirror at a second point aligned with said first point of said center of said concave surface, said pivot bearing means serving as a fulcrum for movement of said mirror holder; and
    a joystick having one end in contact with said concave surface of said mirror holder for varying the inclination of said mirror as a result of joystick movement in contact with said concave surface which in turn moves said mirror holder.

2. A scanning mechanism as claimed in claim 1, further including an adaptor body for mounting said joystick and said mirror holder.

3. A scanning mechanism as claimed in claim 1, said joystick being pivotable about a stick fulcrum.

4. A scanning mechanism as claimed in claim 3, in which a distance between the stick fulcrum and an end of said joystick differs from a radius of curvature of said concave surface.

5. A laser beam scanning adjustment mechanism in which the movement of a joystick is transformed into the inclination of a mirror, comprising;
    a movable mirror holder for holding a mirror and including a concave surface with a first point substantially at the center of said concave surface, pivot bearing means positioned between said mirror holder and said mirror to a second point aligned with said first point of said center of said concave surface, said pivot bearing means serving as a fulcrum for movement of said mirror holder;
    an adaptor body for mounting said joystick and said mirror holder including means for supporting said mirror holder, said supporting means including pivot bearing means engaged with a surface spaced from said concave surface, elastic means connecting said mirror holder and said support means; and
    a joystick having one end in contact with said concave surface of said mirror holder for varying the inclination of said mirror as a result of joystick movement in contact with said concave surface which in turn moves said mirror holder.

6. A scanning mechanism as claimed in claim 5, said elastic means comprising spring means for urging said mirror holder toward said supporting means.

7. A scanning mechanism as claimed in claim 5, said elastic means comprising an elastomer between said mirror holder and said supporting means.

* * * * *